(12) United States Patent
Honebrink et al.

(10) Patent No.: US 6,589,262 B1
(45) Date of Patent: Jul. 8, 2003

(54) LOCKING CATHETER INTRODUCING SYSTEM

(75) Inventors: Brian Honebrink, Stillwater, MN (US); Mark C. Kraus, Independence, MN (US); Eugene Champeau, Plymouth, MN (US)

(73) Assignee: MedAmicus, Inc., Minneapolis, MN (US)

( * ) Notice: Subject to any disclaimer, the term of this patent is extended or adjusted under 35 U.S.C. 154(b) by 0 days.

(21) Appl. No.: 09/540,712

(22) Filed: Mar. 31, 2000

(51) Int. Cl.[7] .............................................. A61M 29/00
(52) U.S. Cl. ...................... 606/191; 604/104
(58) Field of Search .................... 606/191; 604/104, 604/164, 165, 166

(56) References Cited

U.S. PATENT DOCUMENTS

| | | | |
|---|---|---|---|
| 4,233,974 A | 11/1980 | Desecki et al. | 128/215 |
| 4,345,606 A | 8/1982 | Littleford | 128/784 |
| 4,596,559 A | 6/1986 | Fleischhacker | 604/170 |
| 4,682,981 A * | 7/1987 | Suzuki et al. | 604/104 |
| 4,772,266 A * | 9/1988 | Groshong | 604/160 |
| 4,929,236 A | 5/1990 | Sampson | 604/175 |
| 4,966,588 A | 10/1990 | Rayman et al. | 604/165 |
| 5,064,414 A | 11/1991 | Revane | 604/165 |
| 5,098,392 A | 3/1992 | Fleischhacker et al. | 604/165 |
| 5,141,497 A | 8/1992 | Erskine | 604/165 |
| 5,160,323 A | 11/1992 | Andrew | 604/158 |
| 5,171,222 A | 12/1992 | Euteneuer et al. | 604/102 |
| 5,250,033 A | 10/1993 | Evans et al. | 604/160 |
| 5,255,691 A | 10/1993 | Otten | 607/117 |
| 5,275,583 A * | 1/1994 | Crainich | 604/164.12 |
| 5,279,597 A | 1/1994 | Dassa et al. | 503/283 |
| 5,290,294 A | 3/1994 | Cox et al. | 606/108 |
| 5,304,142 A | 4/1994 | Liebl et al. | 604/167 |
| 5,320,602 A | 6/1994 | Karpiel | 604/54 |
| 5,391,152 A * | 2/1995 | Patterson | 604/165.04 |
| 5,437,645 A | 8/1995 | Urban et al. | 604/165 |
| 5,454,790 A * | 10/1995 | Dubrul | 604/104 |
| 5,741,233 A | 4/1998 | Riddle et al. | 604/165 |
| 5,782,807 A | 7/1998 | Falvai et al. | 604/164 |
| 5,827,227 A * | 10/1998 | DeLago | 604/104 |
| 5,879,333 A | 3/1999 | Smith | 604/164 |
| 5,885,217 A * | 3/1999 | Gisselberg et al. | 600/434 |
| 6,120,494 A | 9/2000 | Jonkman | 604/506 |

* cited by examiner

Primary Examiner—Michael J. Milano
Assistant Examiner—Victor Nguyen
(74) Attorney, Agent, or Firm—Schwegman, Lundberg & Woessner & Kluth, P.A.

(57) ABSTRACT

An introducing apparatus includes an elongate tubular sheath having an external diameter small enough to be readily insertable in a selected vein. The sheath has a bore which receives therein a dilator such that a distal end of the dilator projects from out from the distal end of the sheath. A rotatable fastener is rotatably coupled with the dilator, and couples the sheath with the dilator and prevents axial movement therebetween. An anti-rotation member is associated with the dilator and/or the sheath, which prevents the dilator from rotating relative to the sheath as the rotatable fastener is rotated, and also included are means which allow a user to overcome the anti-rotation features without damage to or inadvertent separation the sheath.

20 Claims, 9 Drawing Sheets

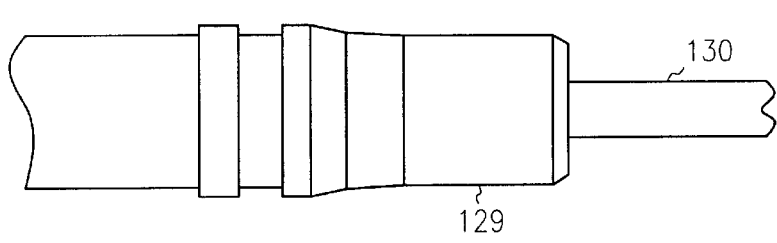
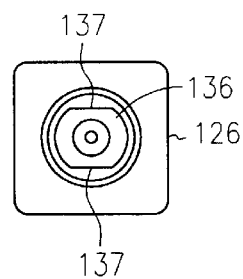
FIG. 5  FIG. 6
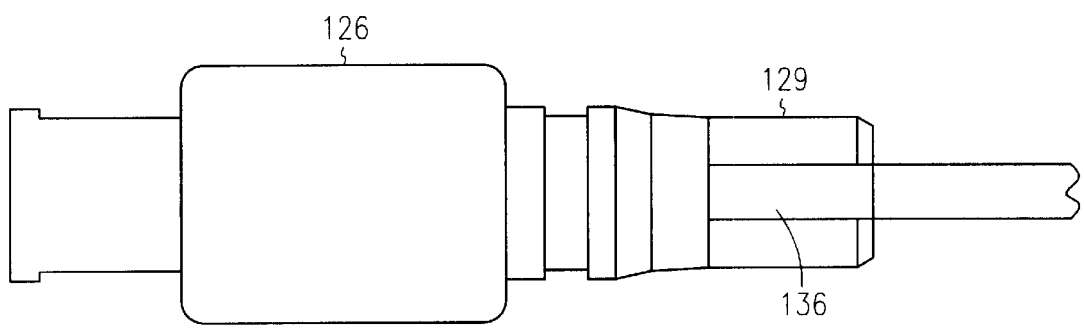
FIG. 7
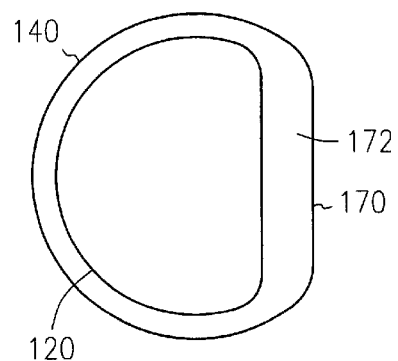
FIG. 8

LOCKING CATHETER INTRODUCING SYSTEM

FIELD OF THE INVENTION

The present invention relates generally to an introducer and dilator for insertion of medical devices into a patient. More particularly, it pertains to an introducer and dilator which lock together.

BACKGROUND OF THE INVENTION

Introducer devices are employed for inserting catheters, guide wires, or other medical devices into patients. A typical procedure provides for insertion of a needle into the vasculature of a patient. After insertion of the needle, a guide wire is inserted through the needle, and the needle is removed. The dilator and the sheath are inserted over the guidewire, and the dilator may be removed leaving the sheath protruding from the patient's vein. A diagnostic or therapeutic catheter (e.g. a central venous access catheter) or guide wire or other medical device, is then inserted through the sheath into the patient.

When the dilator and sheath are inserted over the guidewire, and the medical technician is attempting to drive the dilator through the skin, subcutaneous tissue and the wall of the vein, there is a tendency for the dilator to retract toward the sheath. The retraction of the dilator can result in trauma to the patient, and can also make the implanting process awkward and imprecise for the medical technician. When the dilator recedes to a position where the distal end of the dilator is within the sheath, the relatively large sheath causes a puncture at the entry site which is painfully traumatic to the patient. In addition, there are risks of tearing of the tissue adjacent to the entry site. Further, forcing the sheath into the entry site can result in bending or kinking of the sheath, which can allow the sheath to bend or kink resulting, and a new puncture site would be necessary. Therefore, it is important to lock or fasten the dilator and sheath to each other during the insertion process.

One type of locking device is provided in U.S. Pat. No. 5,879,333, which relates to a catheter which is snap-fitted with a cannula. However, this type of device allows for the cannula to pop out of the catheter unexpectedly, requiring the medical technician to manually hold the dilator and the sheath together during the insertion process despite the presence of the locking device. Another type of locking device is a threaded rotational locking device which locks a dilator to a sheath. However, as the threaded fastener is rotated, the dilator also rotates, resulting in complications and/or distraction to the medical technician during the implant procedure. Other distractions can occur when the medical technician uses a device for a first time, and when damage occurs to the device as a result of misuse.

Accordingly, what is needed is a locking introducer and dilator which do not become easily and/or unintentionally unlocked from one another during or after insertion into a patient. What is further needed is a locking introducer and dilator which do not distract the physician or medical technician during implant.

SUMMARY OF THE INVENTION

An introducing apparatus includes an elongate tubular sheath having an external diameter small enough to be readily insertable in a selected vein. The sheath has a bore which receives therein a dilator such that a distal end of the dilator projects from out from the distal end of the sheath. A rotatable fastener is rotatably coupled with the dilator, and couples the sheath with the dilator and prevents axial movement therebetween. A means of selectively rotating the dilator relative to the sheath includes an anti-rotation member which is associated with the dilator and/or the sheath. The anti-rotation member resists rotational movement of the dilator relative to the sheath as the rotatable fastener is rotated.

In another embodiment, an introducing apparatus includes an elongate tubular sheath having an external diameter small enough to be readily insertable in a selected vein. The sheath has a bore which receives therein a dilator such that a distal end of the dilator projects from out from the distal end of the sheath. A rotatable fastener is rotatably coupled with the dilator, and couples the sheath with the dilator and prevents axial movement therebetween. A hub of the dilator includes an elliptical cross-section which corresponds to the cross-section of the sheath which resists relative rotational movement between the dilator and the sheath.

The introducer assembly allows for the medical technician or physician to rotatably lock the sheath and the dilator to one another without unintentionally rotating one relative to the other during the procedure or during the implant. This improves the implanting process and reduces potential pain or damage to the vasculature of the patient. In addition, the medical technician or physician will not become distracted by components inadvertently rotating or by the components separating from each other. A further benefit includes the ability of the introducer apparatus to withstand damage or separation of the sheath should the medical technician apply excessive torque to the dilator, whether intentional or unintentional. Furthermore, the introducer apparatus allows for the dilator to selectively rotatable without any damage occurring to the sheath and/or the dilator.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 5 is a side elevational view illustrating a portion of the dilator of the introducer apparatus constructed in accordance with one embodiment.

FIG. 6 is a top plan view illustrating a portion of the dilator of the introducer apparatus constructed in accordance with one embodiment.

FIG. 7 is a side elevational view illustrating a portion of the dilator of the introducer apparatus constructed in accordance with one embodiment.

FIG. 8 is a cross-sectional view illustrating a dilator coupled with a sheath constructed in accordance with one embodiment.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
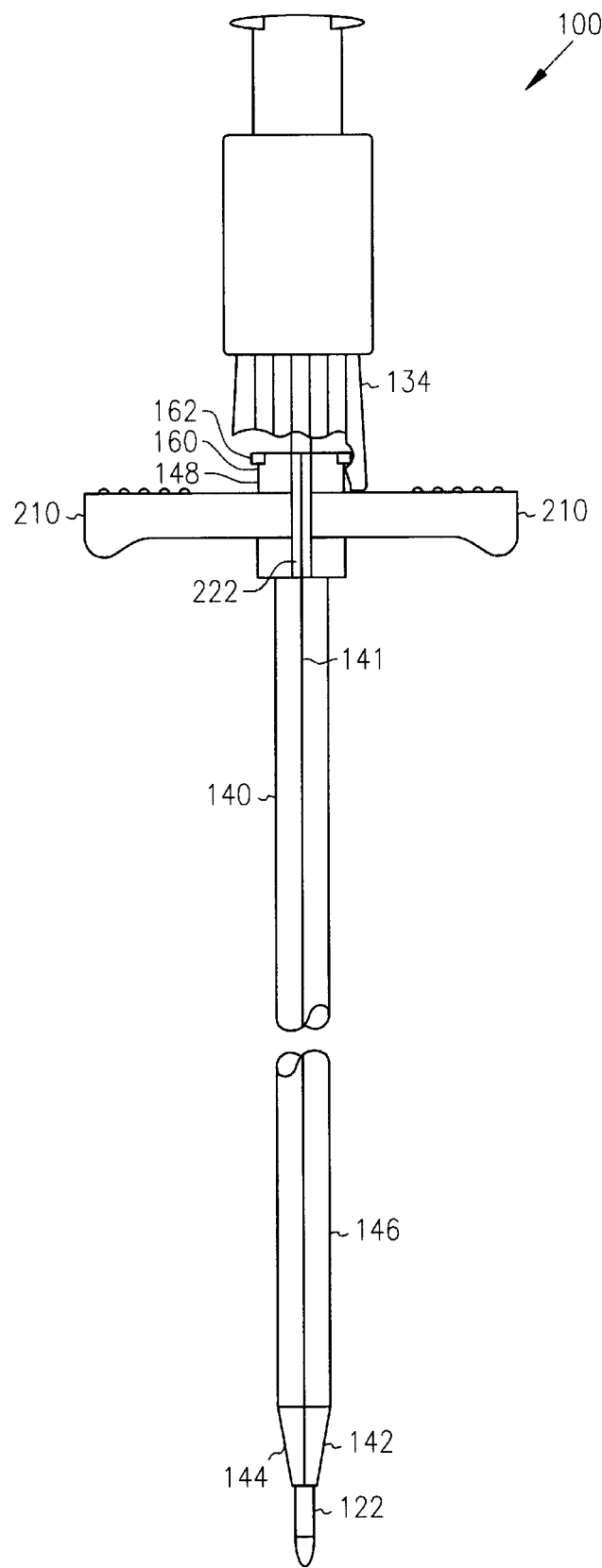
FIG. 1 is a side elevational view illustrating an introducer apparatus constructed in accordance with one embodiment.
Figure 4:
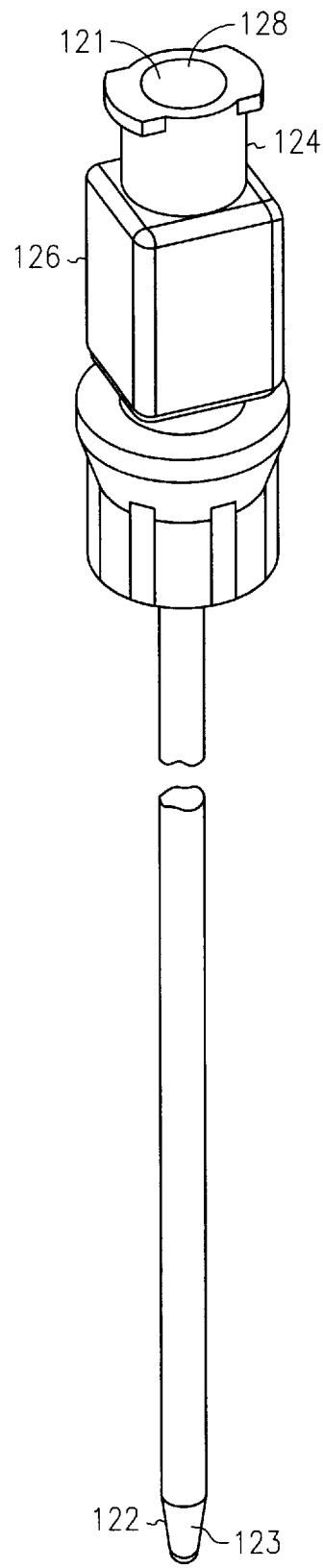
FIG. 4 is a perspective view illustrating a dilator of the introducer apparatus constructed in accordance with one embodiment.

An introducer assembly 100, as shown in FIG. 1, is described herein which includes generally a sheath 140 and a dilator 120. When the sheath 140 and the dilator 120 are assembled, they do not rotate relative to one another as a rotatable fastener is rotated. The dilator 120, as shown in more detail in FIG. 4, allows for the introducer assembly 100 to be introduced into a vein of a patient, for instance, over a guidewire. The dilator 120 extends from a distal end 122 to a proximal end 124, where the distal end 122 is insertable into a patient. The distal end 122 optionally ends in a tapered end 123. At the proximal end 124 is a hub 126 having a bore 128 therethrough. Extending from the hub 126 to the distal end 122 is a generally cylindrical portion 130. The dilator 120 also includes a passage 121 therethrough, aligned with the bore 128, which allows the dilator 120 to be inserted over a guidewire or a catheter. The dilator 120 is sized to be received by the sheath 140 therein.

Figure 2:
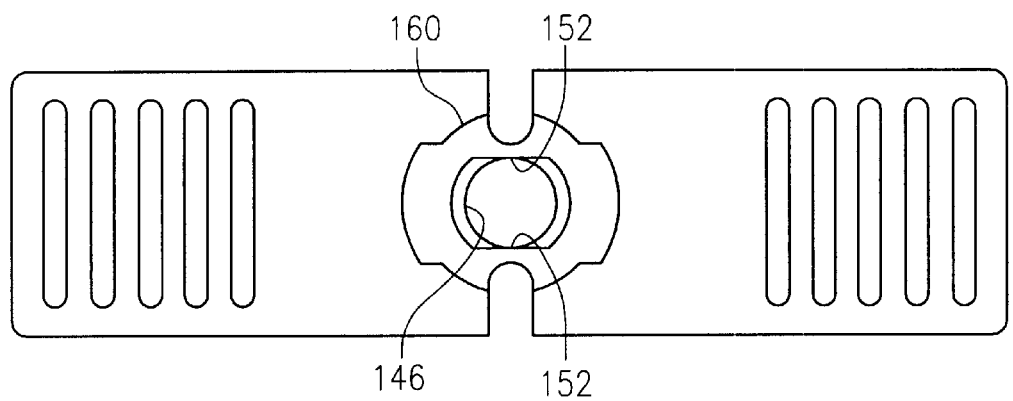
FIG. 2 is a top plan view illustrating a sheath of the introducer apparatus constructed in accordance with one embodiment.
Figure 3:
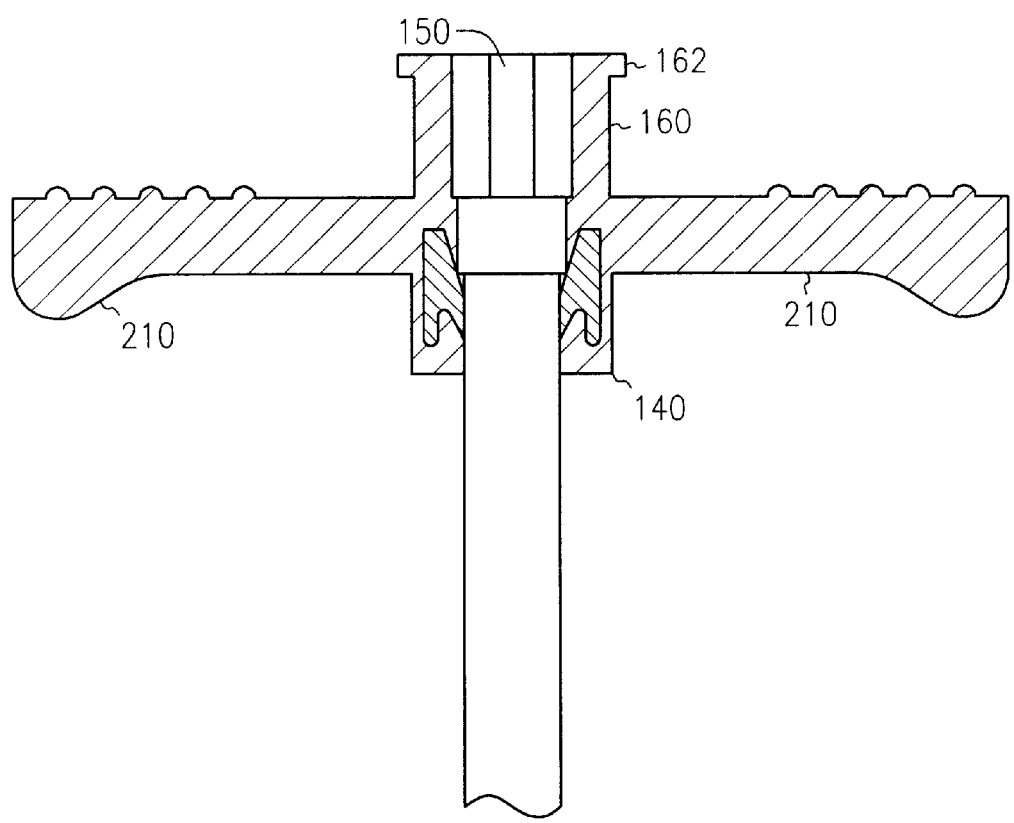
FIG. 3 is a cross-sectional view illustrating a sheath of the introducer apparatus constructed in accordance with one embodiment.

As shown in FIGS. 1–3, the sheath 140 allows for additional instruments to be inserted therethrough and inserted into the patient. The sheath 140 includes various types of sheaths, for instance, the sheath 140 can comprise a sheath which has a strengthening braid of material. Alternatively, the sheath 140 includes those which are modified to prevent bends in the elongate sheath. The sheath 140 extends from a distal end 142 to a proximal end 148, where the distal end 142 is first inserted into the patient and the proximal end 148 remains outside of the patient. Near the distal end 142 is a tapered portion 144 which provides a transition to a cylindrical portion 146. The sheath 140 also includes a passage therethrough which allows for the introduction of the dilator 120 therein. After the introducer assembly 100 has been inserted into a patient, and the dilator 120 is removed, other medical instruments can be easily inserted into and through the sheath 140, and introduced into the patient.

The sheath 140 includes at least one tab 210 which extends radially outward from the sheath 140. In one embodiment, the sheath 140 includes two tabs 220 which are disposed 180 degrees from each other. Disposed between the two tabs 220 are tab break lines 222.

The sheath 140 is splittable such that the sheath 140 is separable into two or more components. The sheath 140 is separable or splittable which prevents disruption to or removal of instruments or devices which have been inserted through the sheath 140. The splittable sheath 140 is splittable in a number of manners such as including at least one score line 141. The sheath 140 is externally scored, and optionally two scores 141 are 180 degrees from each other. The scores 141 are aligned with the tab break lines 222 such that the tab break lines 222 and the scores 141 are disposed between the two tabs 220. Alternatively, the sheath 140 is splittable using a slitting device, a rip cord or strengthening strip running along the longitudinal length of the sheath, a weakening which allows the introducer to be ripped apart, or other techniques which are also to those skilled in the art.

The sheath 140 includes anti-rotation features which prevent the dilator 120 from rotating relative to the sheath 140. In one embodiment, the anti-rotation features include at least one flat 150 disposed within an inner diameter 146 of the sheath 140, as shown in FIGS. 2 and 3. Alternatively, the anti-rotation features include two flats 152. The two flats 152 are sized and positioned to be optionally placed adjacent to anti-rotation features. Other variations on the anti-rotation features are discussed below. At the proximal end 148 of the sheath 140 is a sheath hub 160 to which the dilator 120 is coupled, as further discussed below. The sheath hub 160 includes a lip 162 which facilitates coupling of the dilator 120 thereto. Optionally, the anti-rotation features of the sheath 140 are disposed only within the sheath hub 160.

Referring to again to the dilator 120 as shown in FIG. 1, the dilator 120 includes a rotatable fastener 134 (shown in a cut-away view) rotatably coupled therewith. The rotatable fastener 134 allows for coupling of the dilator 120 to the sheath 140 such that axial movement between the dilator 120 and sheath 140 is prevented. Optionally, the rotatable fastener 134 includes a threaded portion which threadingly engages with the lip 162 of the sheath hub 160. The dilator 120, also shown in FIGS. 4–7, includes a dilator hub 126.

The dilator 120 also includes anti-rotation features. The anti-rotation features are disposed on a coupling portion 129 of the dilator 120. In one embodiment, the anti-rotation features include a flat 136 on the coupling portion 129 of the dilator 120, as shown in FIGS. 5–7. Alternatively, two flats 137 are included on the coupling portion 129 of the dilator 120. The two flats 137 are disposed adjacent to the sheath flats 152 of the introducer apparatus 100 such that, when assembled, the dilator 120 does not rotate relative to the sheath 140.

Figure 9:
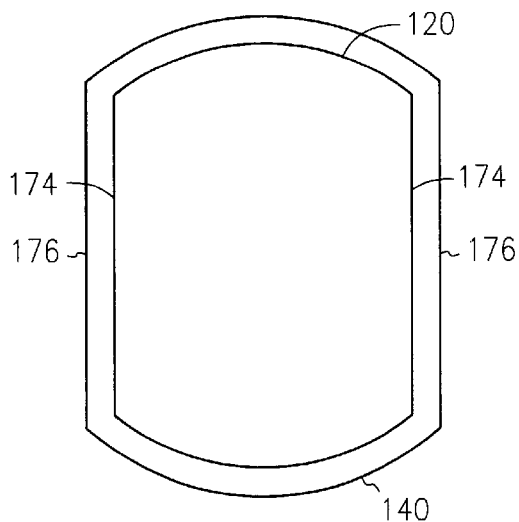
FIG. 9 is a cross-sectional view illustrating a dilator coupled with a sheath constructed in accordance with one embodiment.

Other embodiments of the anti-rotation features of the sheath 140 and/or the dilator 120 are shown in FIGS. 8–11, where a cross-section is shown of the coupling portion 129 of the dilator 120 disposed within the sheath hub 160 of the sheath 140. FIG. 8 illustrates a dilator 120 having a single dilator flat 170 and a sheath 140 having a single sheath flat 172. The dilator flat 170 is disposed adjacent the sheath flat 172. FIG. 9 illustrates a dilator 120 having two dilator flats 174 and a sheath 140 having two sheath flats 176. The two dilator flats 174 are disposed adjacent the two sheath flats 176. It should be noted that more than two flats can be used and is considered within the scope of the invention.

Figure 10:
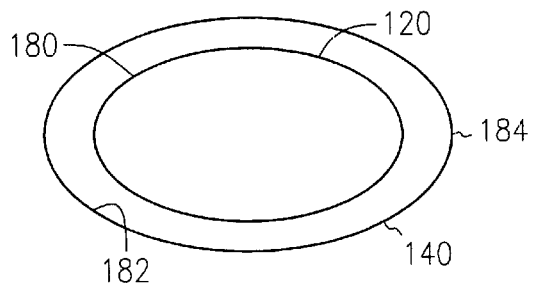
FIG. 10 is a cross-sectional view illustrating a dilator coupled with a sheath constructed in accordance with one embodiment.
Figure 11:
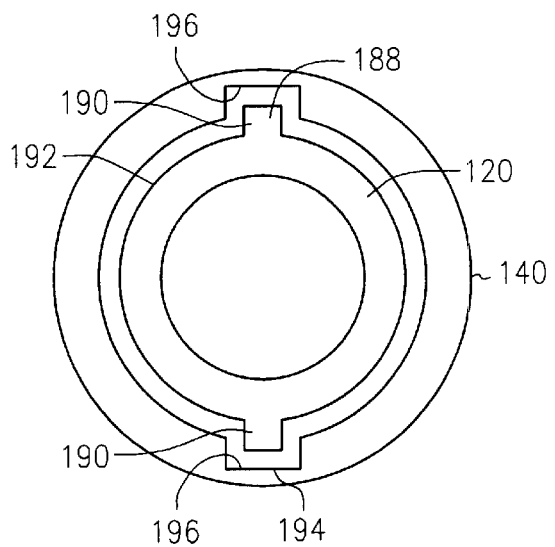
FIG. 11 is a cross-sectional view illustrating a dilator coupled with a sheath constructed in accordance with one embodiment.

FIG. 10 illustrates another embodiment which includes a coupling portion of the dilator 120 having an elliptical cross-section 180 disposed within a sheath 140, where the inner diameter 182 of the sheath has an elliptical cross-section 184. FIG. 11 illustrates yet another alternative. In FIG. 11, the dilator 120 includes at least one projection 188, for instance the dilator 120 includes two projections 190 which project outward from an external surface 192 of the dilator 120. The sheath 140 includes at least one recess 194, for instance, two recesses 196. The recesses are sized and positioned on the inner diameter 182 of the sheath 140 to receive therein the two projections 190 of the dilator 120. During use, the two projections 190 of the dilator 120 are disposed within the recesses 196 of the sheath 140.

To assemble the introducing apparatus 100, the distal end 122 of the dilator 120 is disposed within the sheath 140 until the dilator hub 126 is proximate to the proximal end 148 of the sheath 140. The rotatable fastener 134 is pressed against the lip 162 of the sheath 140 and the rotatable fastener 134 is rotated. As the fastener 134 is rotated, the dilator 120 becomes further inserted into the sheath 140, and becomes axially fixed to the sheath 140 as the threads engage the lip 162 of the sheath 140. In addition, as the fastener 134 is rotated, the anti-rotation features of the dilator 120 and/or the sheath 140 become seated such that further rotation of the rotatable fastener 134 does not cause rotation of the dilator 120 relative to the sheath 140, even when the fastener 134 is rotated to remove the axial fixation of the dilator 120 relative to the sheath 140.

Figure 12:
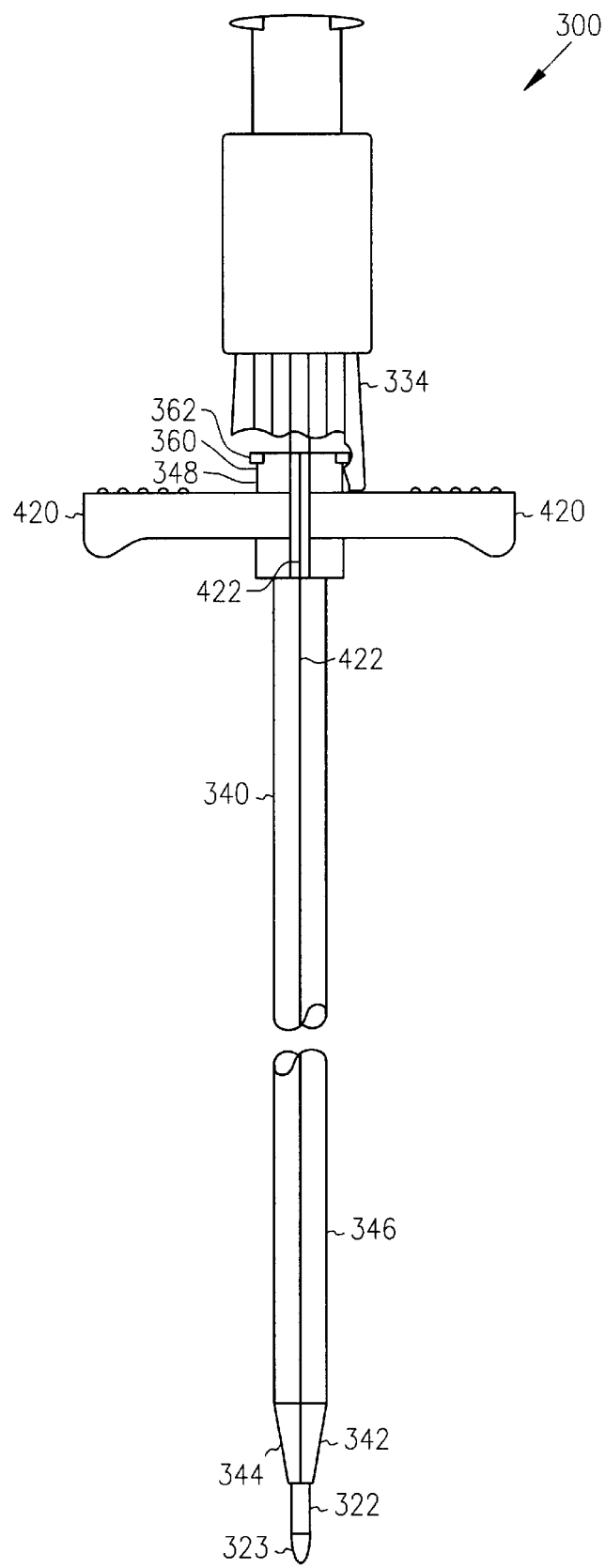
FIG. 12 is a side elevational view illustrating an introducer apparatus constructed in accordance with one embodiment.
Figure 13:
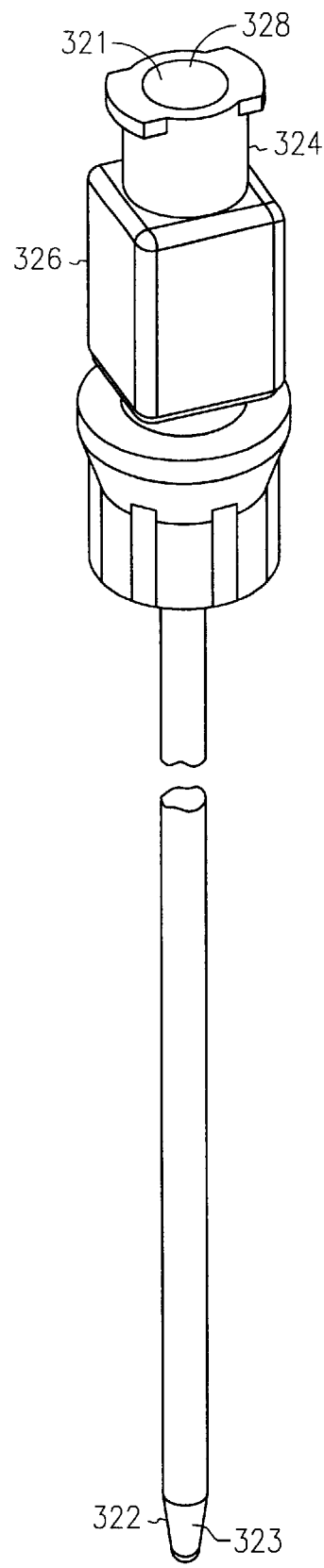
FIG. 13 is a perspective view illustrating a dilator of the introducer apparatus constructed in accordance with one embodiment.

FIG. 12 illustrates another embodiment which shows an introducer assembly 300 including generally a sheath 340 and a dilator 320. When the sheath 340 and the dilator 320 are assembled, a user can selectively choose whether the sheath 340 and the dilator 320 rotate relative to one another, for instance, as a rotatable fastener is rotated. The dilator 320, as shown in more detail in FIG. 13, allows for the introducer assembly 300 to be introduced into a vein of a patient, for instance, over a guidewire. The dilator 320 extends from a distal end 322 to a proximal end 324, where the distal end 322 is insertable into a patient. The distal end 322 optionally ends in a tapered end 323. At the proximal end 324 is a hub 326 having a bore 328 therethrough. Extending from the hub 326 to the distal end 322 is a generally cylindrical portion 330. The dilator 320 also includes a passage 321 therethrough, aligned with the bore 328, which allows the dilator 320 to be inserted over a guidewire or a catheter. The dilator 320 is sized to be received by the sheath 340 therein.

The sheath 340 includes various types of sheaths, for instance, the sheath 340 can comprise a sheath which has a strengthening braid of material. Alternatively, the sheath 340 includes those which are modified to prevent bends in the elongate sheath. The sheath 340 extends from a distal end 342 to a proximal end 348, where the distal end 342 is first inserted into the patient and the proximal end 348 remains outside of the patient. Near the distal end 342 of the sheath 340 is a tapered portion 344 which provides a transition to a cylindrical portion 346. The sheath 340 also includes a passage therethrough which allows for the introduction of the dilator 320 therein. After the introducer assembly 300 has been inserted into a patient, and the dilator 320 is removed, other medical instruments can be easily inserted into and through the sheath 340, and introduced into the patient.

The sheath 340 includes at least one tab 410 which extends radially outward from the sheath 340. In one embodiment, the sheath 340 includes two tabs 420 which are optionally disposed 180 degrees from each other. Disposed between the two tabs 420 are tab break lines 422.

The sheath 340 is splittable such that the sheath 340 is separable into two or more components. The sheath 340 is separable or splittable which prevents disruption to or removal of instruments or devices which have been inserted through the sheath 340. The splittable sheath 340 is splittable in a number of manners such as including at least one score line 341. The sheath 340 is externally scored, and optionally two scores 341 are 180 degrees from each other. The scores 341 are aligned with the tab break lines 422 such that the tab break lines 422 and the scores 341 are disposed between the two tabs 420. Alternatively, the sheath 340 is splittable using a slitting device, a rip cord or strengthening strip running along the longitudinal length of the sheath, a weakening which allows the introducer to be ripped apart, or other techniques which are also to those skilled in the art.

Figure 15:
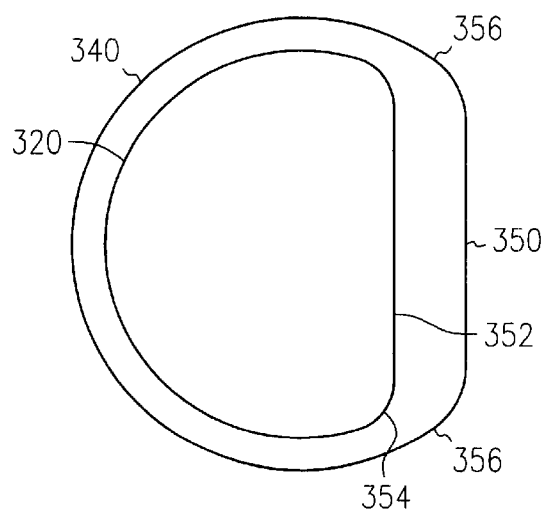
FIG. 15 is a cross-sectional view illustrating a dilator coupled with a sheath constructed in accordance with one embodiment.

The sheath 340 includes anti-rotation features which resist and optionally prevent the dilator 320 from rotating relative to the sheath 340. In addition, additional features allow for the anti-rotation features to be overcome, such that the user can selectively rotate the dilator 320 or can selectively lock the rotational movement of the dilator 320. In one embodiment, the anti-rotation features include at least one flat 350 disposed within an inner diameter of the sheath 340, as shown in FIG. 15, which illustrates a cross-section of the dilator 320 coupled with the sheath 340. Alternatively, the anti-rotation features include two flats. The dilator 320 also includes at least one flat 352, which is disposed adjacent to the sheath flat 350 when the sheath 340 and dilator 320 are locked. The dilator 320 includes rounded edges 354 on the flats 352. Furthermore, the sheath 340 includes rounded corners 356. The rounded edges 354 and the rounded corners 356 allow for a user to overcome the anti-rotation feature without damage to the sheath 340 or the dilator 320 or without unintentional separation of the sheath portions. Optionally, the rounded portions of the dilator and/or sheath could alternatively include tapered edges. Other variations on the anti-rotation features are discussed below.

Referring again to FIG. 12, at the proximal end 348 of the sheath 340 is a sheath hub 360 to which the dilator 320 is coupled, as further discussed below. The sheath hub 360 includes a lip 362 which facilitates coupling of the dilator 320 thereto, such that the dilator 320 can be locked to prevent axial movement between the dilator 320 and the sheath 340. Optionally, the anti-rotation features of the sheath 340 are disposed only within the sheath hub 360.

Figure 14:
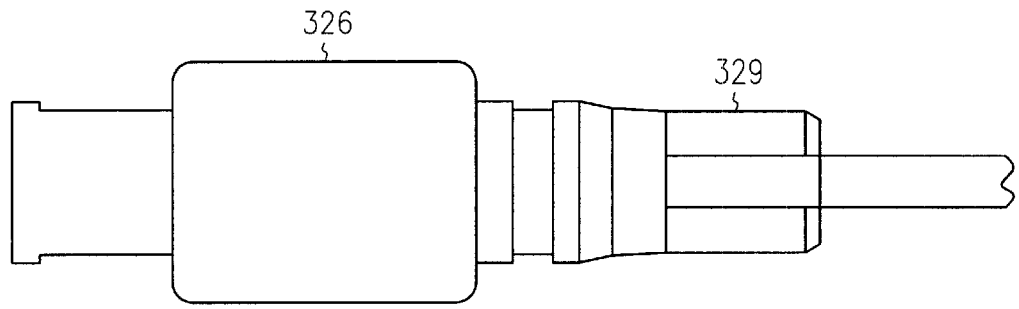
FIG. 14 is a side elevational view illustrating a portion of the dilator of the introducer apparatus constructed in accordance with one embodiment.

Referring to again to the dilator 320 as shown in FIG. 12, the dilator 320 includes a rotatable fastener 334 (shown in a cut-away view) rotatably coupled therewith. The rotatable fastener 334 allows for coupling of the dilator 320 to the sheath 340 such that axial movement between the dilator 320 and sheath 340 is prevented. Optionally, the rotatable fastener 334 includes a threaded portion which threadingly engages with the lip 362 of the sheath hub 360. The dilator 320, also shown in FIGS. 13 and 14, includes a dilator hub 326.

The dilator 320 also includes anti-rotation features. The anti-rotation features are optionally disposed only on the hub 329 of the dilator 320. For example, the hub 329 has an elliptical shape (FIG. 10) which corresponds to the shape of the sheath 340. Other embodiments of the anti-rotation features of the sheath 340 and/or the dilator 320 are shown in FIGS. 15–19, where a cross-section is shown of the hub 326 of the dilator 320 disposed within the sheath hub 360 of the sheath 340. FIG. 15, as discussed above, illustrates a dilator 320 having a single dilator flat 352 and a sheath 340 having a single sheath flat 350. The dilator flat 352 is disposed adjacent the sheath flat 350. It should be noted that more than two flats can be used and is considered within the scope of the invention.

Figure 16:
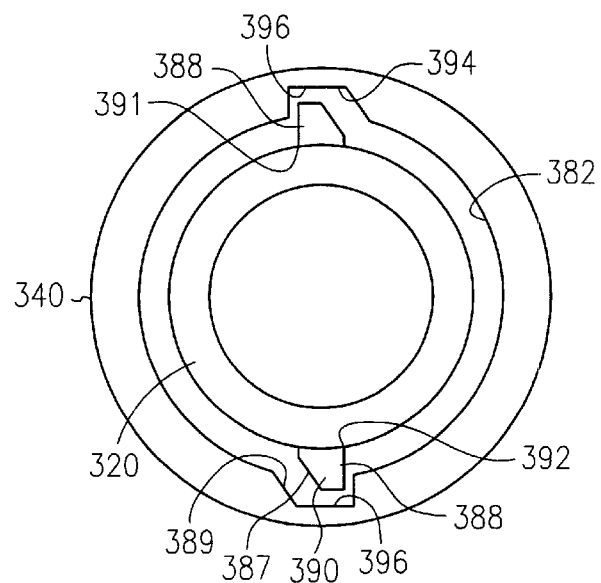
FIG. 16 is a cross-sectional view illustrating a dilator coupled with a sheath constructed in accordance with one embodiment.

FIG. 16 illustrates another embodiment. In FIG. 16, the dilator 320 includes at least one projection 388, for instance the dilator 320 includes two projections 390 which project outward from an external surface 392 of the dilator 320. The projections 390 are adapted to fold about a hinge point 391, such that a selection can be made whether to have the dilator 320 remain in an anti-rotative position or not. The sheath 340 includes at least one recess 394, for instance, two recesses 396. The recesses are sized and positioned on the inner diameter 382 of the sheath 340 to receive therein the two projections 390 of the dilator 320. Optionally, the projections 390 include a tapered edge 387 and the recesses 396 include a tapered edge 389. During use of the anti-rotative features, the two projections 390 of the dilator 320 are disposed within the recesses 396 of the sheath 340.

Figure 17:
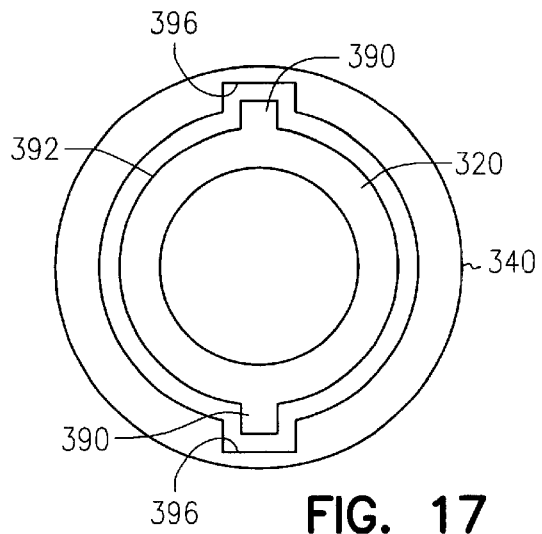
FIG. 17 is a cross-sectional view illustrating a dilator coupled with a sheath constructed in accordance with one embodiment.
Figure 18:
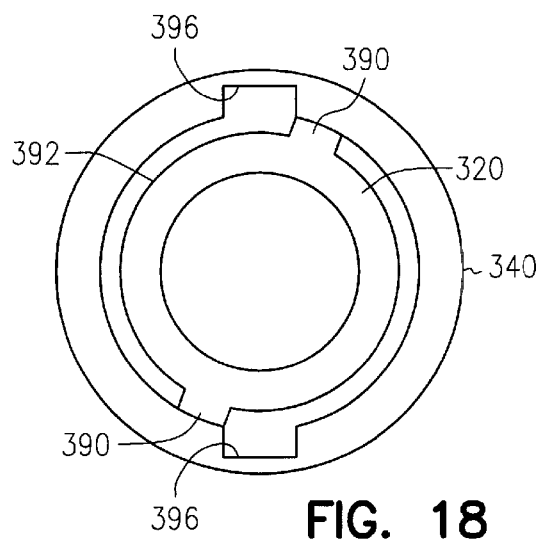
FIG. 18 is a cross-sectional view illustrating a dilator coupled with a sheath constructed in accordance with one embodiment.

FIGS. 17 and 18 illustrate another embodiment. In this embodiment, the dilator 320 includes projections 390 similar to that discussed above, although in addition to or in alternative to the hinge point, the projections 390 are collapsible. For instance, the projections 390 are formed of collapsible material such as foam. FIG. 17 illustrates the projections 390 disposed within the recesses 396 of the sheath 340 in an uncollapsed position. Should the medical technician choose to selectively override these anti-rotation features, the technician applies additional torque which forces the projections to compress, as shown in FIG. 18.

Figure 19:
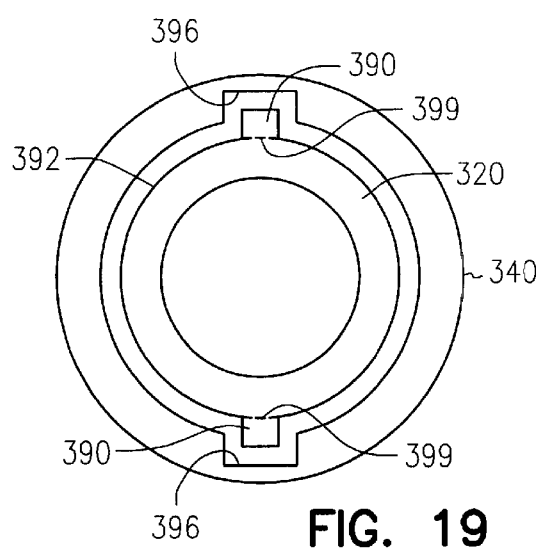
FIG. 19 is a cross-sectional view illustrating a dilator coupled with a sheath constructed in accordance with one embodiment.

FIG. 19 illustrates another embodiment of the introducer apparatus. In this embodiment, the dilator 320 includes projections 390 similar to that discussed above, although in addition to or in alternative to the hinge point, the projections 390 are adapted to break away from the dilator 320. For instance, the projections 390 break away from the external surface 392 of the dilator 320 along a break line 399. The break line 399 can be formed by a score line, for example, or a perforated line. FIG. 19 illustrates the projections 390 disposed within the recesses 396 of the sheath 340, prior to the projections 390 being broken away from the dilator 320. Should the medical technician choose to selectively override these anti-rotation features, the technician applies additional torque which forces the projections 390 to break away from the dilator 320.

To assemble the introducing apparatus 300, the distal end 322 of the dilator 320 is disposed within the sheath 340 until the dilator hub 326 is proximate to the proximal end 348 of the sheath 340. The rotatable fastener 334 is pressed against the lip 362 of the sheath 340 and the rotatable fastener 334 is rotated. As the fastener 334 is rotated, the dilator 320 becomes further inserted into the sheath 340, and becomes axially fixed to the sheath 340 as the threads engage the lip 362 of the sheath 340. In addition, as the fastener 334 is rotated, the anti-rotation features of the dilator 320 and/or the sheath 340 become seated such that further rotation of the rotatable fastener 334 does not cause rotation of the dilator 320 relative to the sheath 340, even when the fastener 334 is rotated to remove the axial fixation of the dilator 320 relative to the sheath 340. However, should the medical technician choose to override the antirotation features, the technician further rotates the dilator 320 relative to the sheath 340 by applying additional torque to unseat the anti rotation features.

Advantageously, the introducer assembly allows for the medical technician or physician to rotatably lock the sheath and the dilator to one another without inadvertently rotating one relative to the other during the procedure or during the implant. This improves the implanting process and reduces potential pain or damage to the vasculature of the patient. In addition, the medical technician or physician will not become distracted by components inadvertently rotating or by the components inadvertently separating from each other. Further benefits provided are that the medical technician can optionally rotate the dilator should they choose to do so without distraction, or without any damage to the sheath or the dilator, or without inadvertently separating a severable sheath.

It is to be understood that the above description is intended to be illustrative, and not restrictive. Many other embodiments will be apparent to those of skill in the art upon reading and understanding the above description. It should be noted that variations shown and described in one embodiment, or one figure can be coupled with other embodiments of the invention. For instance, the anti-rotation features and/or the means for overcoming them can be included on the dilator and/or the sheath. The scope of the invention should, therefore, be determined with reference to the appended claims, along with the full scope of equivalents to which such claims are entitled.

What is claimed is:

1. An introducing apparatus comprising:
   an elongate tubular sheath having an external diameter, the sheath having a bore including an internal diameter sized to receive a dilator therethrough;
   the sheath extending from a distal end and a proximal end;
   the dilator extending from a dilator proximal end to a dilator distal end, the dilator insertable through the proximal end of the bore of the sheath;
   a rotatable fastener rotatably coupled with the dilator, the rotatable fastener for coupling the sheath with the dilator and preventing axial movement therebetween; and
   at least one rotation resisting member positioned on an upper portion of the sheath and on the dilator, the at least one rotation resisting member allowing for selective rotation of the dilator relative to the sheath while the rotatable sheath is rotatably coupled with the fastener.

2. The introducing apparatus as recited in claim 1, further comprising tabs radially extending from the sheath.

3. The introducing apparatus as recited in claim 2, wherein the sheath includes a score line and the sheath is severable at the score line.

4. The introducing apparatus as recited in claim 1, wherein the at least one rotation resisting member is disposed on a hub of the dilator.

5. The introducing apparatus as recited in claim 4, wherein the bore of a sheath hub has an elliptical cross-section and the dilator hub has an elliptical cross-section.

6. The introducing apparatus as recited in claim 1, wherein the bore has at least one sheath flat therein, and the dilator has a dilator flat, where the dilator is disposed in the sheath relative to the sheath such that the dilator flat is adjacent to the sheath flat.

7. The introducing apparatus as recited in claim 6, wherein the dilator flat has rounded edges.

8. The introducing apparatus as recited in claim 1, wherein the dilator further includes at least one collapsible projection and the sheath includes at least one recess disposed within a wall of the bore, and the at least one projection is disposed within the at least one recess.

9. The introducing apparatus as recited in claim 8, wherein the recess has tapered edges.

10. The introducing apparatus as recited in claim 1, wherein the dilator further includes at least one folding projection and the sheath includes at least one recess disposed within a wall of the bore, and the at least one projection is disposed within the at least one recess.

11. The introducing apparatus as recited in claim 1, wherein the rotatable fastener is an internally threaded fastener rotatable relative to the dilator.

12. An introducing apparatus comprising:

an elongate tubular sheath having an external diameter and extending from a proximal end to a distal end, the sheath having a bore including an internal diameter sized to receive a dilator therethrough, the bore extending from the proximal end to the sheath to the distal end of the sheath, the proximal end of the bore having an elliptical cross-section, the distal end of the sheath having a substantially circular cross-section;

the dilator extending from a dilator proximal end to a dilator distal end, the dilator insertable through the proximal end of the bore of the sheath, the dilator distal end having a substantially circular cross-section;

the dilator including a dilator hub at the dilator proximal end, the dilator hub having an elliptical cross-section; and a rotatable fastener rotatably coupled with the dilator, the rotatable fastener for coupling the sheath with the dilator and preventing axial movement therebetween.

13. The introducing apparatus as recited in claim 12, wherein the sheath includes a score line and the sheath is severable at the score line.

14. An introducing apparatus comprising:

an elongate tubular sheath having an external diameter, the sheath having a bore including an internal diameter sized to receive a dilator therethrough, wherein the sheath includes a score line and the sheath is severable at the score line;

the sheath extending a distal end and a proximal end;

the dilator extending from a dilator proximal end to a dilator distal end, the dilator insertable through the proximal end of the bore of the sheath;

a rotatable fastener rotatably coupled with the dilator, the rotatable fastener for coupling the sheath with the dilator and preventing axial movement therebetween; and means for selectively rotating the dilator relative to the sheath without damage to the sheath disposed on a dilator hub and a sheath hub, and distal portions of the dilator and sheath are substantially circular.

15. The introducing apparatus as recited in claim 14, wherein the means for allowing selective rotation comprises at least a portion of the bore having an elliptical cross-section and at least a portion of the dilator having an elliptical cross-section.

16. The introducing apparatus as recited in claim 15, wherein at least a portion of the dilator further includes at least one collapsible projection and at least a portion of the sheath includes at least one recess disposed within a wall of the bore, and the at least one projection is disposed within the at least one recess.

17. The introducing apparatus as recited in claim 14, wherein the means for allowing selective rotation comprises at least a portion of the bore having at least one sheath flat therein, and at least a portion of the dilator having a dilator flat, where the dilator is oriented relative to the sheath such that the dilator flat is placed adjacent to the sheath flat.

18. The introducing apparatus as recited in claim 14, wherein the rotatable fastener is an internally threaded fastener rotatable relative to the dilator.

19. A method comprising:

introducing an introducing apparatus into a vein, wherein the introducing apparatus includes:

an elongate tubular sheath having an external diameter, the sheath having a bore including an internal diameter sized to receive a dilator therethrough;

the sheath extending a distal end and a proximal end;

the dilator extending from a dilator proximal end to a dilator distal end, the dilator insertable through the proximal end of the bore of the sheath;

a rotatable fastener rotatably coupled with the dilator, the rotatable fastener for coupling the sheath with the dilator and preventing axial movement therebetween;

at least one rotation resisting member positioned on an upper portion of the sheath and on the dilator, the at least one rotation resisting member allowing for selective rotation of the dilator relative to the sheath while the rotatable sheath is rotatably coupled with the fastener;

selectively rotating the dilator relative to the sheath without separating the sheath;

rotating the rotatable fastener; and fastening the dilator to the sheath to prevent axial movement of the dilator relative to the sheath.

20. The method as recited in claim 19, wherein rotating the rotatable fastener includes rotating an internally threaded fastener relative to the dilator.

* * * * *